United States Patent
Jeong et al.

(10) Patent No.: US 9,557,273 B2
(45) Date of Patent: Jan. 31, 2017

(54) QUANTITATIVE ANALYZING METHOD OF CIGS FILM USING A LASER INDUCED BREAKDOWN SPECTROSCOPY

(71) Applicant: GWANGJU INSTITUTE OF SCIENCE AND TECHNOLOGY, Gwangju (KR)

(72) Inventors: Sungho Jeong, Gwangju (KR); Jeong Hwan In, Gwangju (KR); Chan Kyu Kim, Gwangju (KR); Seokhee Lee, Gwangju (KR); Hakjae Lee, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 520 days.

(21) Appl. No.: 14/143,723

(22) Filed: Dec. 30, 2013

(65) Prior Publication Data

US 2014/0336971 A1    Nov. 13, 2014

(30) Foreign Application Priority Data

May 8, 2013  (KR) .................. 10-2013-0052152

(51) Int. Cl.
*G01C 19/00* (2013.01)
*G01D 18/00* (2006.01)
(Continued)

(52) U.S. Cl.
CPC ........... *G01N 21/718* (2013.01); *Y02E 10/541* (2013.01); *Y02E 10/543* (2013.01)

(58) Field of Classification Search
CPC ........ Y02E 60/122; Y02E 10/50; Y02E 60/13; Y02E 10/542; Y02E 60/721; Y02E 10/52; Y02E 10/541; Y02E 20/16; Y02E 20/18; Y02E 60/528; H01M 10/052; H01M 10/0525; H01M 10/0565; H01M 2220/20; B60L 11/18; B60L 11/1803; B60L 11/1809; B60L 11/1811; B60L 11/1824; B60L 11/184; B60L 11/1846; B60L 15/20; B60L 15/2009; B60L 2210/30; B60L 2210/40; B60L 2230/22; B60L 2240/12

See application file for complete search history.

(56) References Cited

U.S. PATENT DOCUMENTS

| | | | |
|---|---|---|---|
| 2012/0029836 A1* | 2/2012 | Hermann ................ | G01J 3/443 702/28 |
| 2012/0099103 A1* | 4/2012 | Hahn .................... | G01N 21/718 356/316 |
| 2013/0155404 A1* | 6/2013 | Jeong ................... | G01N 21/718 356/318 |

OTHER PUBLICATIONS

V. Probst et al., Siemens AG Corporate Research and Development, (The Impact of Controlled Sodium Incorporation on Rapid Thermal Processed Cu(InGa)Se2—Thin Films and Devices), p. 144-147, Dec. 5-9, 1994, IEEE.

(Continued)

*Primary Examiner* — Roy Y Yi
(74) *Attorney, Agent, or Firm* — Hauptman Ham, LLP

(57) ABSTRACT

Disclosed herein is a quantitative analyzing method of a copper indium gallium selenide (CIGS) film, the method including: obtaining spectra by irradiating a laser on the plurality of CIGS films having different component compositions, selecting a first spectral line and a second spectral line among the spectra of target elements to be analyzed and obtaining a correlation plot between a measured intensity of the first spectral line and a measured intensity of the second spectral line, correcting the measured intensity of the first spectral line and the measured intensity of the second spectral line using results obtained by curve fitting the correlation plot, obtaining a linear calibration curve using (Continued)

the corrected intensity of the first spectral line and the corrected intensity of the second spectral line; and comparing the linear calibration curve with LIBS analysis of a target sample to be analyzed.

5 Claims, 6 Drawing Sheets

(51) Int. Cl.
*G01F 25/00* (2006.01)
*G06F 19/00* (2011.01)
*G01N 21/71* (2006.01)

(56) References Cited

OTHER PUBLICATIONS

Tokio Nakada et al., Effects of Sodium on Cu(In, Ga)Se2-Based Thin Films and Solar Cells, (Jpn. J. Appl. Phys. vol. 36 (1997) Part 1, No. 2), p. 732-737, Feb. 1997, Department of Electrical Engineering and Electronics.
A. Rockett, The Electronic effects of point defects in Cu(In$x$Ga1-$x$)Se2, p. 330-337 and 361-362, Department of Materials Science, University of Illinois, (Thin Solid Films).

\* cited by examiner

FIG. 2

| | SMS | AES | SEMEDS | XRF | GD-MS | LIBS |
|---|---|---|---|---|---|---|
| Depth profiling resolution | 1-20 nm | 10-100 Å | 0.5-2 micron | >1 micron | 100 to 300 nm | 30 to 100 nm |
| Lateral resolution | >10 micron | 0.01-2 micron | 0.2 to 2 micron | 10 micron to 1 mm | >1000 micron | 10 micron |
| Measurement time for 2 micron film | hours | hours | minutes | minutes | 10's minutes to hr | seconds |
| Detection limit | ppb | 1000 to 10000 ppm | 1000 to 10000 ppm | 100 to 1000 ppm | Sub-ppm | ppm |
| Sample preparation | Minor sectioning to put into the sample holder | Little sample prep but the sample needs to be conductive | Coating with C or Au | Minor palletizing or little prep | Minor surfacing cleaning or little sample prep; mainly conductive sample | Little sample prep |
| Measurement environment | High vacuum | High vacuum | High vacuum | In air | High vacuum | In air in chamber with buffer gas |
| Elemental coverage | Most of elements in the periodic table | Most of elements in the periodic table (except H & He) | Difficult for light elements | Difficult for light elements like H, N, C, B, Be, Li | Most of elements in the periodic table | Most of elements in the periodic table |
| Instrument cost | 500K to 1 Mil USD | 250 to 500K USD | 500 to 750K USD (with SEM) | 50 to 150K USD | 400 to 800 K USD | 120 to 170K USD |

▓▓▓ Depth profiling for thin film structure difficult
▭▭▭ Requires high vacuum and expensive instrument cost

QUANTITATIVE ANALYZING METHOD OF CIGS FILM USING A LASER INDUCED BREAKDOWN SPECTROSCOPY

CROSS REFERENCE TO RELATED APPLICATION

This application claims the benefit of Korean Patent Application No. 10-2013-0052152, filed on May 8, 2013, which is hereby incorporated by reference in its entirety into this application.

BACKGROUND OF THE INVENTION

1. Technical Field

The present invention relates to a quantitative analyzing method of a copper indium gallium selenide (CIGS) film using a laser induced breakdown spectroscopy.

2. Description of the Related Art

Plasma generated by laser irradiation emits light having a specific wavelength depending on the material on which the laser is irradiated. As a result, components of the material may be qualitatively or quantitatively analyzed by collecting the light. A laser induced breakdown spectroscopy (hereinafter, referred to as LIBS), which is one method of analyzing the components of the material using the collected light, is a spectroscopic analysis technology using plasma produced by generating breakdown, which is a kind of discharge phenomenon, using a high output laser, as an excitation source. A sample is vaporized in the plasma induced by the laser, such that atoms and ions may be present in an excited state. The atoms and ions in the excited state release energy after a lifespan and return back to a ground state. In this case, the atoms and ions emit light having a unique wavelength according to the kind of elements and the excited state. Therefore, when analyzing a spectrum of the emitted light, the components of the material may be qualitatively or quantitatively analyzed.

FIG. 1 is an illustration view showing an operation principle of LIBS according to the related art.

Referring to FIG. 1, first, in the case in which an ablation (a phenomenon in which the material is removed while being melted and evaporated by the laser) is performed for a material having a very small quantity (several μg) by irradiating a pulse laser, as in Step 102, the ablated material absorbs laser energy to thereby cause ionization in a very short time (typically, in several nanoseconds), and to form high temperature plasma of about 15000 K or more as in Step 104. When a laser pulse is stopped, the respective elements present in the plasma emit specific spectra corresponding thereto while the high temperature plasma is cooled. In this case, by collecting and analyzing the emitted spectra using a spectrometer as in Step 106, unique spectrum data of each element may be obtained as in Step 108 and component composition and quantity of substance contained in the material may be measured by analyzing the spectrum data.

The LIBS technology is different from other measuring technologies in that 1) an entire time spent on measuring is within 1 second, 2) a separate sampling and pre-conditioning process for the measurement is not required, 3) since only a very small quantity (several μg) of material is consumed for one measurement, an elementary composition of the material may be measured precisely to nm unit while the material is ablated in a depth direction, 4) a separate environment for the measurement is not required and the measurement may be performed under air atmosphere, 5) all elements except for an inert gas may be analyzed in ppm precision, and 6) an instrument may be configured at relatively low costs.

FIG. 2 is a chart comparing the LIBS with other measuring technologies.

Referring to FIG. 2, since a secondary ion mass spectrometry (SIMS), an atomic emission spectroscopy (AES), an energy dispersive X-ray spectroscopy (EDS), a glow discharge mass spectrometry (GD-MS), and the like which are frequently used in measuring a substance distribution need to be performed under high vacuum, it is only possible to measure in a laboratory specific to the invention thereof and it is impossible to practically apply to a production line. Since an inductively coupled plasma mass spectrometry (ICP-MS) which is widely used other than those mentioned above has difficulty in that a piece to be analyzed needs to be melted in a solvent and should then be analyzed, it is also impossible to apply to the production line. Currently, an X-ray fluorescence (XRF), which is widely used for analyzing substance of a solar cell material in the laboratory or in the field due to simplicity of use is relatively inexpensive and may be measured under air atmosphere, but has a technical limitation in measuring the substance distribution of a copper indium gallium selenide (CIGS) film in that ① since light elements such as Na, O, N, C, B, Be, Li, and the like are hardly measured, it is impossible to measure a Na content in the CIGS film, which has a decisive effect on a component efficiency, ② the XRF has a precision in a depth direction of at most about 1 μm, it is impossible to measure the element distribution in the depth direction in the CIGS film having a thickness of 2 μm, and ③ it is difficult to determine whether a fluorescence signal to be measured is output from a practical film or a substrate.

In general, a semiconductor solar cell refers to a device of directly converting solar light into electricity using a photovoltaic effect in which electrons are generated when irradiating light on a semiconductor diode comprised of a p-n junction. As most basic configuration components, there are three portions such as a front electrode, a back contact electrode, and a light absorbing layer disposed therebetween. Among these, the most important material is the light absorbing layer that determines most of photoelectric transformation efficiency, and the solar cell is classified into various kinds according to the above-mentioned material. Particularly, a CIGS film solar cell refers to that in which the material of the light absorbing layer is made of Cu(In, Ga)Se$_2$ which is a I-II-VI$_2$ compound. The CIGS film solar cell, which is a high efficiency and low cost type solar cell, has recently been competitively marketed globally, has been prominent as the surest second-generation solar cell replacing a crystalline silicon solar cell in a solar cell field, and represents efficiency closest to a single crystalline silicon component, which is the maximal efficiency of 20.6%.

FIG. 3 is an illustration view schematically showing a structure of the CIGS film solar cell.

FIG. 4 is a flow chart schematically showing a process of manufacturing a CIGS film module.

Firstly, the CIGS film solar cell is manufactured by sequentially depositing a Mo layer, a CIGS layer, a CdS layer, and a TCO layer on a substrate. A detailed description thereof is as follows. The CIGS film module is manufactured by firstly depositing Mo, which is a back contact electrode layer on the substrate, forming (P1 scribing) a pattern by a scribing process, sequentially depositing the CIGS layer (the absorbing layer) and a CdS buffer layer on the Mo layer having the pattern formed thereon, forming (P2 scribing) a pattern by the scribing process, then sequentially depositing a transparent conductive oxide (TCO) layer and a front electrode grid made of Ni/Al on the CdS layer, and finally forming (P3 scribing) a pattern by performing the scribing process. The scribing process as described above is a process performing the patterning so as to be connected in series at a constant interval in order to prevent a decrease in efficiency due to an increase in a sheet resistance while an area of the solar cell is increased, and is performed over a total of three times, that is, P1, P2, and P3. According to the related art, the P1 scribing process performs the patterning using a laser, and the P2 and P3 scribing processes perform the patterning using a mechanical method, but a technology in which all of the P1, P2, and P3 scribing processes perform the patterning using the laser has been recently developed.

In a case of the CIGS film solar cell as described above, it has been reported that a thickness (1 to 2.2 μm) of the film, a structure of the device, a composition of substance configuring the CIGS film which is a multinary compound, and an element distribution in the film have a decisive effect on light absorption and photoelectric transformation efficiency, that sodium (Na) diffused into a CIGS light absorbing layer from soda-lime glass which is widely used as the substrate during the process increases a charge concentration of the film (Nakada et al., Jpn. J. Appl. Phys., 36, 732 (1997)) or increases a CIGS single grain size to thereby decrease structural characteristic variation according to a composition change and improve photoelectric transformation efficiency (Rockett et al., Thin Solid Films 361-362 (2000), 330; Probst et al., Proc of the First World Conf. on Photovoltaic Energy, Conversion (IEEE, New York, 1994), p 144). The reports as mentioned above show that chemical properties of the light absorbing layer need to be controlled by measuring the substance distribution in the film in order to manage quality in the production line of the CIGS film solar cell.

Meanwhile, a continuous production process of the CIGS film solar cell is mainly classified into a roll-to-plate (hereinafter, referred to as R2P) process using a hard material substrate such as the soda-lime glass and a roll-to-roll (hereinafter, referred to as R2R) process using a soft material substrate such as a metal thin plate such as stainless steel, Ti, Mo, or Cu, a polymer film such as polyimide, or the like. At a current time in which the present application is filed, a line of the continuous production process is not provided with a system capable of measuring physical and chemical properties of the CIGS film having the decisive effect on performance of the product in real time, such that physical and chemical properties as mentioned above cannot but depend on values which are pre-determined in a research and development phase. In addition, even though the physical and chemical properties are deviated from a physical and chemical standard targeted by a practical production process, it is impossible to separately check, and the deviated physical and chemical properties cannot but be found through degradation in performance and quality in a phase of evaluating the final completed product, thereby causing significant loss of the product. The continuous production process as described above requires considerable effort and time in order to detect a physical and chemical variable causing the degradation in performance and quality of the product, thereby causing an increase in price and degradation in competitiveness. Therefore, a development of a process control system capable of measuring physical and chemical properties of the CIGS film formed in real time without the pre-conditioning process in the continuous production process line has been urgently demanded.

Meanwhile, in the case of measuring properties of the CIGS film by LIBS, a light generated from an atom of plasma induced by a laser is absorbed by other circumjacent atoms, such that an intensity of the light may be decreased. In the case of generating a self-absorption phenomenon, an intensity of a spectrum of a target element to be measured is non-linearly changed according to concentration thereof. As a result, a degree of precision of the measured value becomes decreased.

SUMMARY OF THE INVENTION

An object of the present invention is to provide a quantitative analyzing method of a copper indium gallium selenide (CIGS) film using a linear calibration curve correcting an effect of a self-absorption at the time of analyzing a laser induced breakdown spectroscopy (LIBS).

According to an exemplary embodiment of the present invention, there is provided a quantitative analyzing method of a copper indium gallium selenide (CIGS) film, the method including: obtaining spectra by irradiating a laser on the plurality of CIGS films having different component compositions, selecting a first spectral line and a second spectral line among the spectral lines of target elements to be analyzed and obtaining a correlation plot between a measured intensity of the first spectral line and a measured intensity of the second spectral line, correcting the measured intensity of the first spectral line and the measured intensity of the second spectral line using results obtained by curve fitting the correlation plot, obtaining a linear calibration curve using the corrected intensity of the first spectral line and the corrected intensity of the second spectral line; and comparing the linear calibration curve with LIBS analysis of a target sample to be analyzed.

An upper energy level of the first spectral line may be the same as that of the second spectral line.

A relationship between the measured intensity ($J'_1$) and the corrected intensity ($J_1$) of the first spectral line may be represented by the following Equation (1):

$$J'_1 = J_1 \left[ \frac{1 - \exp(-J_1 C_1)}{J_1 C_1} \right]^\beta \qquad (1)$$

a relationship between the measured intensity ($J'_2$) and the corrected intensity ($J_2$) of the second spectral line may be represented by the following Equation (2):

$$J'_2 = \alpha J_2 \left[ \frac{1 - \exp(-J_2 C_2)}{J_2 C_2} \right]^\beta \qquad (2)$$

a ratio between $C_1$ and $C_2$ may be represented by the following Equation (3):

$$\frac{C_2}{C_1} = \frac{\lambda_2^5}{\lambda_1^5} \exp\left( \frac{hc/\lambda_2 - hc/\lambda_1}{k_B T} \right) \frac{\lambda_1^2 \Delta v_1}{\lambda_2^2 \Delta v_2} \qquad (3)$$

$$= \frac{\lambda_2^3}{\lambda_1^3} \exp\left( \frac{E_{1,l} - E_{2,l}}{k_B T} \right)$$

$$\equiv \eta(T)$$

($E_{1,l}$ and $E_{2,l}$ are lower energy levels), and a ratio between $J_1 C_1$ and $J_2 C_2$ may be represented by the following Equation (4):

$$\frac{J_2 C_2}{J_1 C_1} = \frac{g_2 A_2 \lambda_2^2}{g_1 A_1 \lambda_1^2} \exp\left(\frac{E_{1,t} - E_{2,t}}{k_B T}\right) \equiv \rho(T). \tag{4}$$

The measured intensity ($J'_2$) of the second spectral line may be represented by the following Equation (5):

$$J'_2 = F(\alpha, \eta, \rho, C_1, J'_1) \tag{5}$$

The correcting of the measured intensity of the first spectral line and the measured intensity of the second spectral line may include obtaining unknown values of Equation (5) by curve fitting the correlation plot using the Equation (5).

BRIEF DESCRIPTION OF THE DRAWINGS

FIG. 2 is a chart comparing the LIBS with other measuring technologies;

DESCRIPTION OF THE EXEMPLARY EMBODIMENTS

Figure 1:
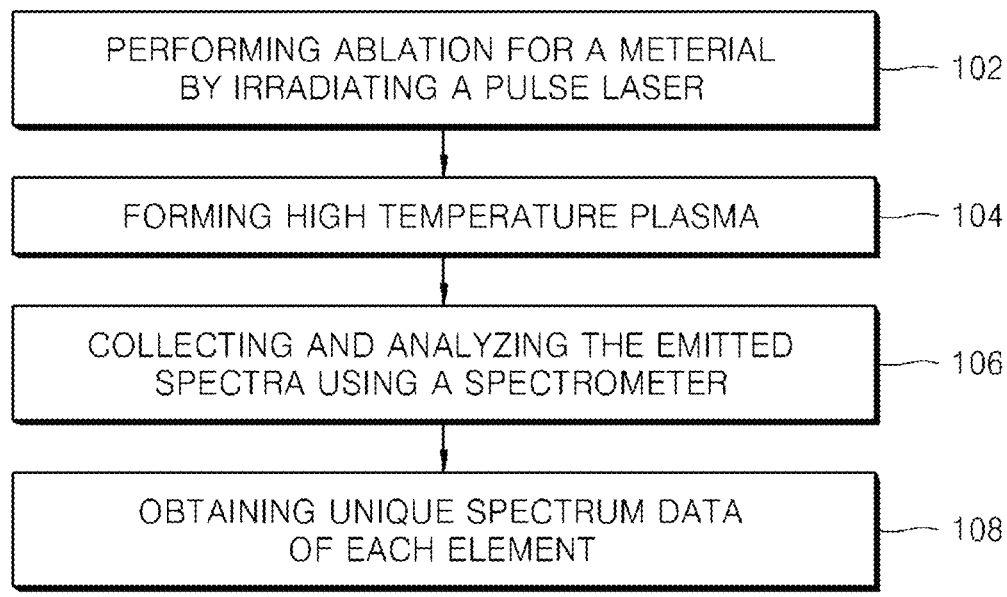
FIG. 1 is an illustration view showing an operation principle of LIBS according to the related art.
Figure 3:
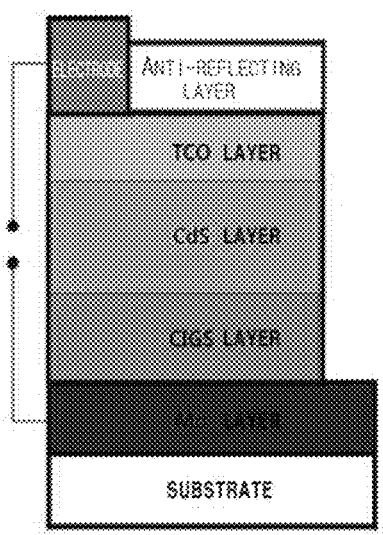
FIG. 3 is an illustration view schematically showing a structure of a CIGS film solar cell.
Figure 4:
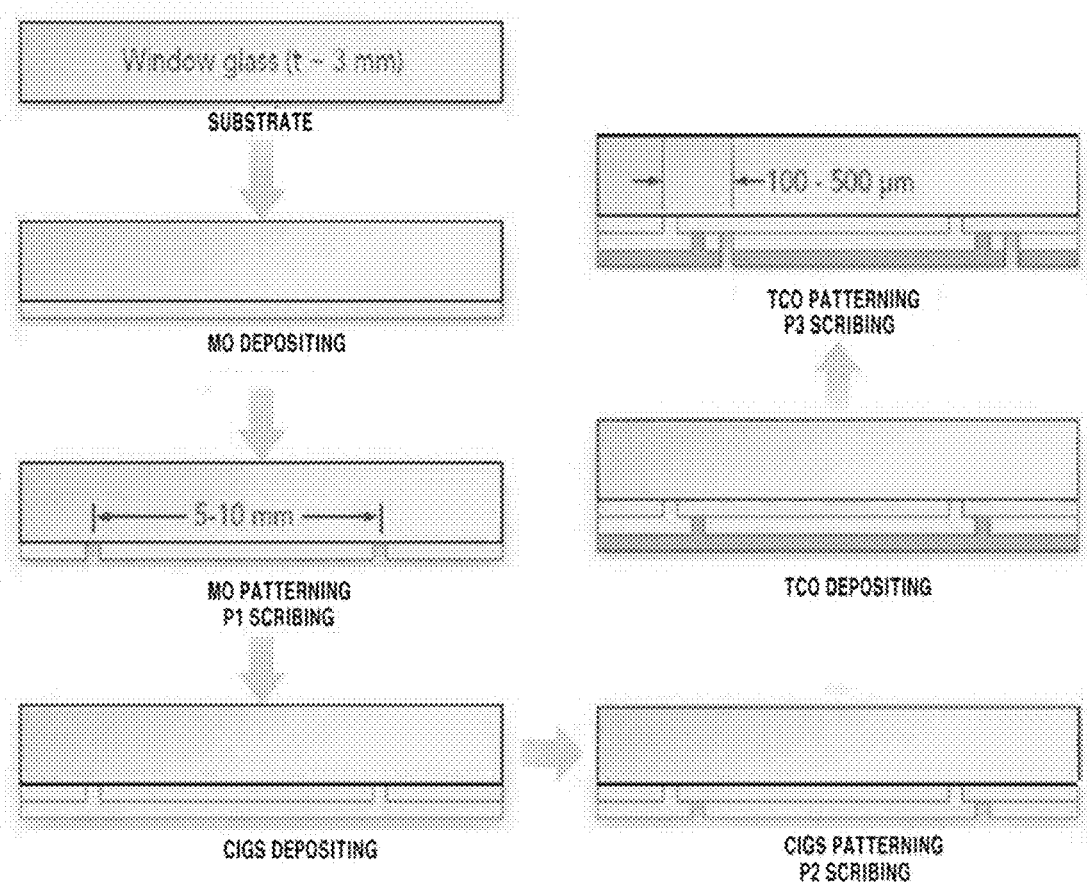
FIG. 4 is a flow chart schematically showing a process of manufacturing a CIGS film module.

Hereinafter, exemplary embodiments of the present invention will be described in detail with reference to the accompanying drawings. Like reference numerals designate like components in the description and the accompanying drawings and an overlapped description will be omitted. In addition, if it is determined in describing examples of the present invention that the detail description of relevant known functions or components makes subject matters of the present invention obscure, the detailed description thereof will be omitted.

It is to be understood that when one element is referred to as being "connected to" or "coupled to" another element, it may be connected directly to or coupled directly to another element or be connected to or coupled to another element, having the other element intervening therebetween. On the other hand, it is to be understood that when one element is referred to as being "connected directly to" or "coupled directly to" another element, it may be connected to or coupled to another element without the other element intervening therebetween.

Unless explicitly described to the contrary, a singular form may include a plural form in the present specification. The word "comprises" or "comprising," will be understood to imply the inclusion of stated constituents, steps, operations and/or elements but not the exclusion of any other constituents, steps, operations and/or elements.

In the case of performing a laser induced breakdown spectroscopy (LIBS) analysis, a light generated from an atom of plasma induced by a laser is absorbed by other circumjacent atoms, such that an intensity of the light is decreased. It is known that a correlation between a measuring intensity (J') of a spectral line affected by the above-described self-absorption and an intensity (J) of a spectral line obtained by correcting the self-absorption may be represented by the following Equation (1):

$$J' = J\left[\frac{1 - \exp(-JC)}{JC}\right]^\beta \tag{1}$$

in Equation (1), $\beta$, which is a variable introduced for convenience in calculation, may be varied depending on cases. For example, $\beta$ may be 0.44, 0.46 or 0.5. Meanwhile, J and C are represented by the following Formulas (2) and (3):

$$J \equiv \frac{hc}{4\pi\lambda_0} A_{ki} n_k l S_0 \tag{2}$$

$$\begin{aligned} C &\equiv \frac{\lambda_0^5}{2hc^2} \frac{n_i g_k}{n_k g_i}\left(1 - \frac{n_k g_i}{n_i g_k}\right)\frac{2}{\pi \Delta \lambda S_0} \\ &\approx \frac{\lambda_0^5}{2hc^2} \exp\left(\frac{hc/\lambda_0}{k_B T}\right)\frac{2}{\pi \Delta \lambda S_0} \\ &= \lambda_0^5 \exp\left(\frac{hc/\lambda_0}{k_B T}\right)\frac{1}{w n_e S_0} \times const. \end{aligned} \tag{3}$$

wherein h is a Planck's constant, $\lambda_0$ is the center wavelength of a spectral line, c is a speed of light, $k_B$ is a Boltzmann's constant, T is plasma temperature, $\Delta\lambda$ is a Stark broadening of a spectral line, w is an electron impact half width of a spectral line, $n_e$ is an electron density, $S_0$ is a cross-sectional area when it is assumed that plasma is homogeneous rod, $A_{ki}$ is a transition probability of a spectral line, $n_k$ is atom density at an energy level k, and l is a length of a plasma rod.

In the case in which there are two spectral lines affected by the self-absorption, intensities measured from two spectral lines may be represented by the following Equations (4) and (5):

$$J'_1 = J_1\left[\frac{1 - \exp(-J_1 C_1)}{J_1 C_1}\right]^\beta \tag{4}$$

$$J'_2 = \alpha J_2\left[\frac{1 - \exp(-J_2 C_2)}{J_2 C_2}\right]^\beta \tag{5}$$

wherein suffixes 1 and 2 represent two measured spectral lines, respectively, a is a detector calibration factor of $J_2$. In this case, the detector calibration factor of $J_1$ is assumed to be 1, which is because that a ratio of a correcting factor rather than a value of an individual correcting factor is meaningful. Meanwhile, in the case in which upper energy levels of two spectral lines are the same as each other, it may be assumed that stark broadening between them are the same as each other ($\Delta\lambda = \lambda^2 \Delta v/c$, $\Delta v_1 = \Delta v_2$). Therefore, a ratio between $C_1$ and $C_2$ may be deduced from Equation (3) and the ratio is represented by the following Equation (6):

$$\begin{aligned} \frac{C_2}{C_1} &= \frac{\lambda_2^5}{\lambda_1^5} \exp\left(\frac{hc/\lambda_2 - hc/\lambda_1}{k_B T}\right)\frac{\lambda_1^2 \Delta v_1}{\lambda_2^2 \Delta v_2} \\ &= \frac{\lambda_2^3}{\lambda_1^3} \exp\left(\frac{E_{1,t} - E_{2,t}}{k_B T}\right) \\ &\equiv \eta(T) \end{aligned} \tag{6}$$

in Equation (6), $E_{1,l}$ and $E_{2,l}$ are lower energy levels.

Meanwhile, a ratio between $J_1C_1$ and $J_2C_2$ deduced from Equations (2) and (3) is represented by the following Equation (7):

$$\frac{J_2C_2}{J_1C_1} = \frac{g_2 A_2 \lambda_2^2}{g_1 A_1 \lambda_1^2} \exp\left(\frac{E_{1,l} - E_{2,l}}{k_B T}\right) \quad (7)$$

$$\equiv \rho(T)$$

As shown in Equation (5), $J'_2$ is a function of a, $C_2$ and $J_2$, and $C_2$ is $\eta C_1$ and $J_2$ is $J_1\eta/\rho$. Since $J_1$ is a function of $C_1$ and $J'_1$, $J'_2$ may be represented by a function of a, $\eta$, $\rho$, $C_1$ and $J'_1$ as shown in the following Equation (8):

$$J'_2 = F(\alpha, \eta, \rho, C_1, J'_1) \quad (8).$$

from Equation (8), in the case in which a plasma temperature is known, $\eta$ and $\rho$ may be calculated from Equations (6) and (7), remaining unknown parameters are a and $C_1$. a and $C_1$ may be calculated by applying Equation (8) to a correlation plot between intensities of two spectral lines using a non-linear least square fitting method.

Meanwhile, a $C_1$ value obtained by the above-described calculation is an average value. Referring to Equation (3), since $C_1$ is a function between density and temperature of plasma, $C_1$ may also be represented by the following functions of density or temperature of plasma:

$$C_1 = C_{1,mean}$$

$$C_1(N_e) = \frac{C_{1,mean} N_{e,mean}}{N_e}$$

wherein $N_{e,mean}$ and $T_{mean}$ are an average density and an average temperature of plasma. In addition, $E_{1,h}$ is an upper energy level and $E_{1,l}$ is a lower energy level. Similar to this, from Equation (6) above, $C_2$ may be represented by the following Equations:

$$C_2 = \eta_{mean} C_{1,mean}$$

$$C_2(N_e) = \frac{\eta_{mean} C_{1,mean} N_{e,mean}}{N_e}$$

$$C_2(T) = \frac{C_{1,mean}}{\exp((E_{1,h} - E_{1,l})/k_B T_{mean})} \exp\left(\frac{E_{2,h} - E_{2,h}}{k_B T}\right) \frac{\lambda_2^3 \Delta v_1}{\lambda_1^3 \Delta v_2}$$

$$C_2(N_e, T) = \frac{C_{1,mean} N_{e,mean}}{\exp((E_{1,h} - E_{1,l})/k_B T_{mean})} \frac{\exp((E_{2,h} - E_{2,l})/k_B T)}{N_e} \frac{\lambda_2^3 \Delta v_1}{\lambda_1^3 \Delta v_2}$$

wherein, $E_{2,h}$ is an upper energy level and $E_{2,l}$ is a lower energy level.

As described above, in the case in which $C_1$, $C_2$, and a values are calculated, $J_1$ and $J_2$ may be calculated from $J'_1$ and $J'_2$ obtained by Equations (4) and (5), respectively, and a linear calibration curve may be obtained. In addition, component compositions of target samples to be analyzed may be analyzed by comparing the thus-obtained linear calibration curve with LIBS analysis results of target samples to be analyzed (for example: a CIGS film).

EXAMPLE

Nine CIGS samples having different component compositions, respectively, were prepared and used for a LIBS analysis. Each component composition and thickness of each sample was measured by X-ray fluorescence (XRF).

TABLE 1

| Sample | Concentration (at %) | | | | Se/Cu Concentration | CIGS | CIGS Deposition |
|---|---|---|---|---|---|---|---|
| No. | Cu | In | Ga | Se | Ratio | Thickness | Method |
| 1 | 24.91 (±0.17) | 8.93 (±0.05) | 13.55 (±0.08) | 52.61 (±0.20) | 2.11 (±0.02) | 1.55 | Co-evaporation |
| 2 | 22.94 (±0.13) | 14.01 (±0.14) | 8.79 (±0.07) | 54.26 (±0.10) | 2.37 (±0.01) | 2.49 | |
| 3 | 24.05 (±0.14) | 13.24 (±0.16) | 9.06 (±0.11) | 53.65 (±0.09) | 2.23 (±0.01) | 2.65 | |
| 4 | 24.59 (±0.15) | 12.94 (±0.16) | 8.94 (±0.09) | 53.53 (±0.20) | 2.18 (±0.02) | 2.52 | |
| 5 | 29.25 (±0.29) | 16.88 (±0.14) | 0.22 (±0.06) | 53.65 (±0.25) | 1.83 (±0.03) | 0.75 | Sputtering |
| 6 | 30.85 (±0.49) | 16.42 (±0.18) | 0.22 (±0.06) | 52.52 (±0.34) | 1.70 (±0.04) | 0.66 | |
| 7 | 31.73 (±0.46) | 16.16 (±0.37) | 0.17 (±0.06) | 51.93 (±0.20) | 1.64 (±0.03) | 0.68 | |
| 8 | 31.51 (±0.48) | 16.26 (±0.34) | 0.11 (±0.05) | 52.12 (±0.22) | 1.65 (±0.03) | 0.70 | |
| 9 | 29.56 (±0.36) | 16.35 (±0.23) | 0.26 (±0.06) | 53.83 (±0.23) | 1.82 (±0.03) | 0.80 | |

-continued $$C_1(T) = \frac{C_{1,mean}}{\exp((E_{1,h} - E_{1,l})/k_B T_{mean})} \exp\left(\frac{E_{1,h} - E_{1,l}}{k_B T}\right)$$

$$C_1(N_e, T) = \frac{C_{1,mean} N_{e,mean}}{\exp((E_{1,h} - E_{1,l})/k_B T_{mean})} \frac{\exp((E_{1,h} - E_{1,l})/k_B T)}{N_e}$$

LIBS spectra at 30 laser irradiation points were collected, the total 60 spectra were obtained, and an average value thereof was obtained and used in the LIBS analysis of each sample. Se spectral lines at wavelengths of 196.089 nm and 203.984 nm were selected among them. As shown in the following Table 2, the upper energy levels of the selected Se spectral lines at wavelengths of 196.089 nm and 203.984 nm are the same as 6.3228 eV. Meanwhile, Cu spectral lines used to presume temperature and density of plasma are shown in the following Table 2.

TABLE 2

| Element | Ionization State | λ (nm) | $E_i$ (eV) | $E_k$ (eV) | $A_{ki}$ | $g_i$ | $g_k$ | $A_{ki}g_k$ |
|---|---|---|---|---|---|---|---|---|
| Se | I | 196.089 | 0.0000 | 6.3228 | 2.13E8 | 5 | 3 | 6.39E8 |
|    |    | 203.984 | 0.2467 | 6.3228 | 9.80E7 | 3 | 3 | 2.94E8 |
| Cu | I | 261.837 | 1.3889 | 6.1227 | 3.07E7 | 6 | 4 | 1.23E8 |
|    |    | 282.437 | 1.3889 | 5.7527 | 7.80E6 | 6 | 6 | 4.68E7 |
|    | II | 227.626 | 2.9754 | 8.4206 | 5.40E7 | 3 | 3 | 1.62E8 |
|    |    | 236.989 | 3.2564 | 8.4864 | 4.80E7 | 5 | 7 | 3.36E8 |

Figure 5:
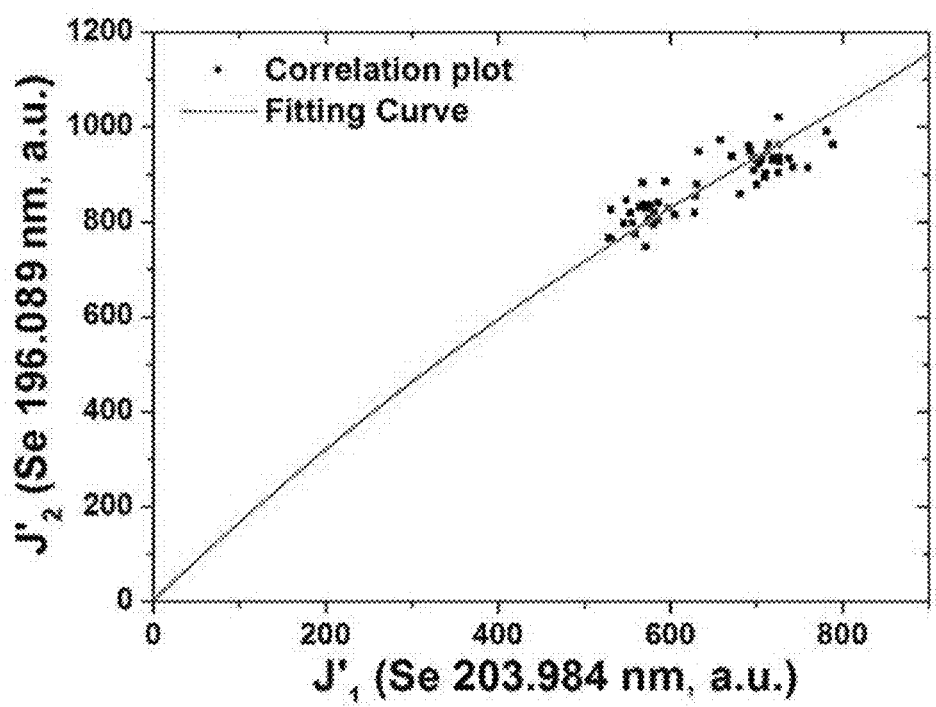
FIG. 5 is a graph showing a correlation plot and a curve fitting of intensities of Se spectral lines at wavelengths of 196.089 nm and 203.984 nm.

FIG. 5 is a graph showing a correlation plot and a curve fitting of intensities of Se spectral lines at wavelengths of 196.089 nm and 203.984 nm. Optimal values of $C_1$ and a calculated by nonlinear least square fitting were 0.00135 and 0.778, respectively. Meanwhile, the $C_1$ value determined by the calculation was an average value.

Self-absorption corrected Se spectral lines ($J_1$ and $J_2$) may be calculated by using the $C_1$ and a values obtained as described above. The total atom density of Se in the plasma was calculated by using the corrected spectral line intensities and the presumed plasma temperature and density.

Meanwhile, in order to judge reliability of the quantitative analyzing method according to the embodiment of the present invention, a calibration curve regarding a ratio of spectral line intensities of Se and Cu was made out. To this end, the total atom density of Cu was also calculated by the same method as described above using Cu spectral line intensities at wavelengths of 261.837 nm and 282.437 nm. Results obtained from 30 irradiation points were averaged to obtain a $R_{Se/Cu}$ which is an averaged species density ratio.

Figure 6:
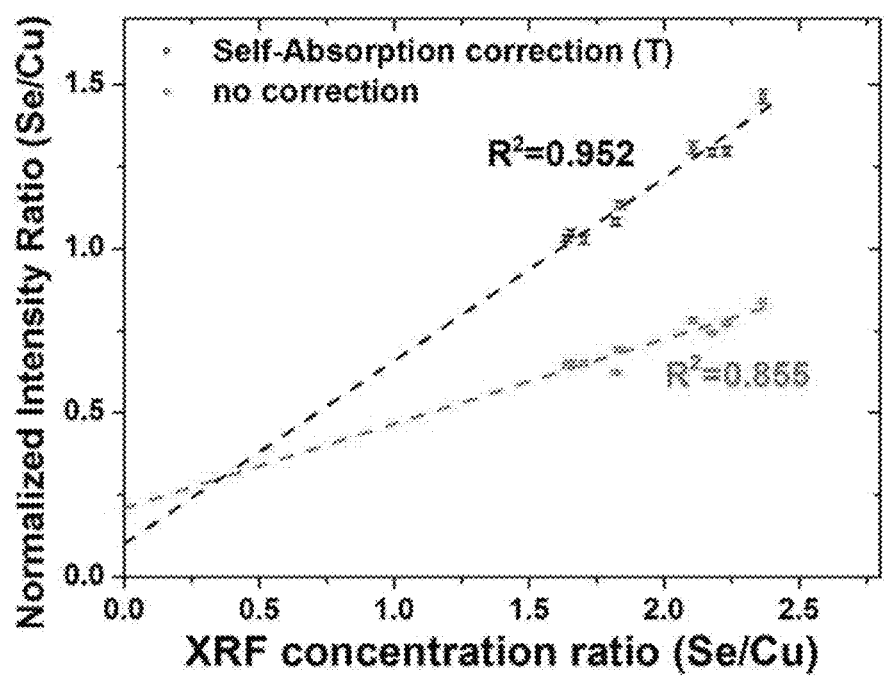
FIG. 6 is a graph showing a calibration curve of a Se/Cu ratio.

FIG. 6 is a graph showing a calibration curve of a Se/Cu ratio.

Referring to FIG. 6, a coefficient of correlation ($R^2$) of a normalized Se/Cu intensity ratio and a Se/Cu concentration ratio measured by XRF was 0.952 in the normalized calibration curve through the self-absorption correction. Meanwhile, the coefficient of correlation in the normalized calibration curve without the self-absorption correction was 0.855, which was lower than that in the normalized calibration curve through the self-absorption correction.

Meanwhile, σ/S (σ is a standard deviation of a ratio of a spectral line intensity and S is a slope of the calibration curve) is an index showing precision of the calibration curve, and the smaller the σ/S value is, the higher a degree of precision is. σ/S in the normalized calibration curve through the self-absorption correction was 0.0697. Meanwhile, σ/S in the normalized calibration curve without the self-absorption correction was 0.0709, which was higher than that in the normalized calibration curve through the self-absorption correction.

In summary, the coefficient of correlation of the normalized calibration curve through the self-absorption correction according to the embodiment of the present invention was higher than that of the normalized calibration curve without the self-absorption correction, and σ/S of the normalized calibration curve through the self-absorption correction was lower than that of the normalized calibration curve without the self-absorption correction. In conclusion, it could be appreciated that the degree of measuring precision of the normalized calibration curve through the self-absorption correction according to the embodiment of the present invention was increased.

With the quantitative analyzing method of the CIGS film according to the embodiment of the present invention, high reliability may be obtained by using the linear calibration curve correcting the effect of the self-absorption at the time of analyzing the laser induced breakdown spectroscopy (LIBS).

The spirit of the present invention has been just exemplified. It will be appreciated by those skilled in the art that various modifications, changes, and substitutions can be made without departing from the essential characteristics of the present invention. Accordingly, the embodiments disclosed in the present invention and the accompanying drawings are used not to limit but to describe the spirit of the present invention. The scope of the present invention is not limited only to the embodiments and the accompanying drawings. The protection scope of the present invention must be analyzed by the appended claims and it should be analyzed that all spirit within a scope equivalent thereto are included in the appended claims of the present invention.

What is claimed is:

1. A quantitative analyzing method of a copper indium gallium selenide (CIGS) film, the method comprising:
    obtaining spectra by irradiating a laser on the plurality of CIGS films having different component compositions,
    selecting a first spectral line and a second spectral line among the spectral lines of target elements to be analyzed and obtaining a correlation plot between a measured intensity of the first spectral line and a measured intensity of the second spectral line,
    correcting the measured intensity of the first spectral line and the measured intensity of the second spectral line using results obtained by curve fitting the correlation plot,
    obtaining a linear calibration curve using the corrected intensity of the first spectral line and the corrected intensity of the second spectral line; and
    comparing the linear calibration curve with LIBS analysis of a target sample to be analyzed.

2. The method of claim 1, wherein an upper energy level of the first spectral line is the same as that of the second spectral line.

3. The method of claim 2, wherein
    a relationship between the measured intensity ($j'_1$) and the corrected intensity ($J_1$) of the first spectral line is represented by the following Equation (1):

$$J'_1 = J_1 \left[ \frac{1 - \exp(-J_1 C_1)}{J_1 C_1} \right]^\beta \quad (1)$$

a relationship between the measured intensity ($J'_2$) and the corrected intensity ($J_2$) of the second spectral line is represented by the following Equation (2):

$$J'_2 = \alpha J_2 \left[ \frac{1 - \exp(-J_2 C_2)}{J_2 C_2} \right]^\beta \quad (2)$$

a ratio between $C_1$ and $C_2$ is represented by the following Equation (3):

$$\frac{C_2}{C_1} = \frac{\lambda_2^5}{\lambda_1^5} \exp\left( \frac{hc/\lambda_2 - hc/\lambda_1}{k_B T} \right) \frac{\lambda_1^2 \Delta v_1}{\lambda_2^2 \Delta v_2} \quad (3)$$

$$= \frac{\lambda_2^3}{\lambda_1^3} \exp\left(\frac{E_{1,l} - E_{2,l}}{k_B T}\right)$$

$$\equiv \eta(T) \quad (5)$$

($E_{1,l}$ and $E_{2,l}$ are lower energy levels), and
a ratio between $J_1C_1$ and $J_2C_2$ is represented by the following Equation (4):

$$\frac{J_2 C_2}{J_1 C_1} = \frac{g_2 A_2 \lambda_2^2}{g_1 A_2 \lambda_1^2} \exp\left(\frac{E_{1,l} - E_{2,l}}{k_B T}\right) \equiv \rho(T). \quad (4)$$

4. The method of claim 3, wherein the measured intensity ($J'_2$) of the second spectral line is represented by the following Equation (5):

$$J'_2 = F(\alpha, \eta, \rho, C_1, J'_1) \quad (5).$$

5. The method of claim 4, wherein the correcting of the measured intensity of the first spectral line and the measured intensity of the second spectral line includes obtaining unknown values of the Equation (5) by curve fitting the correlation plot using the Equation (5).

* * * * *